United States Patent
Chang

(10) Patent No.: US 10,261,031 B2
(45) Date of Patent: Apr. 16, 2019

(54) MASK INSPECTION DEVICE AND METHOD THEREOF

(71) Applicant: ACEMACH CO., LTD, New Taipei (TW)

(72) Inventor: Chih-Chiang Chang, New Taipei (TW)

(73) Assignee: Acemach Co., Ltd., New Taipei (TW)

( * ) Notice: Subject to any disclaimer, the term of this patent is extended or adjusted under 35 U.S.C. 154(b) by 354 days.

(21) Appl. No.: 15/346,430

(22) Filed: Nov. 8, 2016

(65) Prior Publication Data

US 2017/0131218 A1 May 11, 2017

(30) Foreign Application Priority Data

Nov. 9, 2015 (TW) .............................. 104136819 A

(51) Int. Cl.
*G01N 21/94* (2006.01)
*G01C 3/08* (2006.01)
(Continued)

(52) U.S. Cl.
CPC ............... *G01N 21/94* (2013.01); *G01C 3/08* (2013.01); *G01N 15/0227* (2013.01); *G01N 15/1456* (2013.01); *G01N 21/95* (2013.01); *G01N 21/956* (2013.01); *G06T 7/0008* (2013.01); *H04N 5/23296* (2013.01); *G01N 15/0612* (2013.01);
(Continued)

(58) Field of Classification Search
CPC .. G01N 21/94; G01N 21/956; G01N 15/0227; G01N 21/95; G01N 15/1456; G01N 2021/95676; G01N 15/0612; G01N 2015/03; G01N 2201/06113; G01C 3/08; G06T 7/0008; G06T 2207/30148; H04N 5/23296

See application file for complete search history.

(56) References Cited

U.S. PATENT DOCUMENTS 4,513,316 A * 4/1985 Kobayashi ............. G01N 21/88
348/133
5,531,632 A * 7/1996 Mizutani ................. B24B 49/12
451/6

(Continued)

FOREIGN PATENT DOCUMENTS

JP          10176918 A  *  6/1998
JP        2004296829 A  * 10/2004
WO    WO-2006007727 A1 *  1/2006 ......... G01B 11/0608

*Primary Examiner* — Sathyanaraya V Perungavoor
*Assistant Examiner* — Philip P. Dang
(74) *Attorney, Agent, or Firm* — Wang Law Firm, Inc.

(57) ABSTRACT

Provided herein is a mask inspection device, including an inspection base, a shift platform, a rotating platform, a bearing platform, a laser ranging module, a vertical shift module, a processing module, and an image capturing module. A mask, which is carried and held by the bearing platform, includes a dust-proof film, each region of which is measured by the laser ranging module for generating a distance measuring signal; each distance measuring signal is utilized to control the movement of the vertical shift module, such that image capturing module can take an inspection image of that region. Based on the distance measuring signals and inspection images, height information of the dust-proof film and inspection information can be acquired. Also provided herein is a method applicable to said mask inspection device.

9 Claims, 5 Drawing Sheets

(51) Int. Cl.
  *G01N 15/02* (2006.01)
  *G01N 15/14* (2006.01)
  *G01N 21/95* (2006.01)
  *G06T 7/00* (2017.01)
  *H04N 5/232* (2006.01)
  *G01N 21/956* (2006.01)
  *G01N 15/06* (2006.01)
  *G01N 15/00* (2006.01)

(52) U.S. Cl.
  CPC . *G01N 2015/03* (2013.01); *G01N 2015/0693* (2013.01); *G01N 2021/95676* (2013.01); *G01N 2201/06113* (2013.01); *G06T 2207/30148* (2013.01)

(56) References Cited

U.S. PATENT DOCUMENTS

| | | | |
|---|---|---|---|
| 7,068,350 B2* | 6/2006 | Nishi | G03F 7/70425 355/53 |
| 7,728,968 B2* | 6/2010 | Tsai | G01N 21/8806 356/237.2 |
| 8,352,886 B2* | 1/2013 | Laske | G03F 1/64 430/5 |
| 8,435,703 B2* | 5/2013 | Sekihara | G03F 1/64 430/5 |
| 8,497,476 B2* | 7/2013 | Hatakeyama | G01N 23/2251 250/310 |
| 8,593,632 B1* | 11/2013 | Shibazaki | G03F 7/70775 355/53 |
| 8,796,621 B2* | 8/2014 | Hatakeyama | H01J 37/244 250/306 |
| 2009/0309022 A1* | 12/2009 | Gunji | G01N 23/2251 250/307 |
| 2011/0075120 A1* | 3/2011 | Ichinose | G03F 7/70766 355/53 |
| 2012/0212484 A1* | 8/2012 | Haddick | G02B 27/0093 345/419 |

* cited by examiner

MASK INSPECTION DEVICE AND METHOD THEREOF

CROSS-REFERENCE TO RELATED APPLICATION

This application claims priority from Taiwan Patent Application No. 104136819, filed on Nov. 9, 2015 in the Taiwan Intellectual Property Office, the content of which is hereby incorporated by reference in its entirety for all purposes.

BACKGROUND OF THE INVENTION

1. Field of the Invention

The present invention relates to a mask inspection device and the method thereof, and particularly relates to a mask inspection device and the method thereof that the particle inspection can be performed on the dust-proof film on the frame of the mask, and, through the measurement of the distance to adjust the vertical position, the accurate inspection image for each inspection region can be acquired to correspondingly generate the height information of the dust-proof film as well as the inspection information.

2. Description of the Related Art

In the current technology of semiconductor fabrication, circuit patterns of a semiconductor device are formed on the surface of a wafer by printing them through a mask or a reticle.

As the dimension of semiconductor devices shrinks, the defects of the mask, such as pattern distortion or malformation, can greatly impact the quality of circuit patterns on a silicon wafer during manufacturing semiconductor devices. The most commonly known cause of defects is particles that are attached on the surface of the mask.

In order to maintain its quality during the application, the mask is conventionally covered with a mask protection pellicle on its surface to prevent the falling particles directly attached to the mask. However, particles can be attached on the dust-proof film, which is included in the mask protection pellicle, during its disposition, and then possibly falls on the surface of the mask during the operation or the transportation.

Therefore, how to inspect and identify whether there are particles attached on the surface of the dust-proof film of the mask protection pellicle is a considerably urgent issue in the associated industry to be dealt with.

SUMMARY OF THE INVENTION

In view of the issue of the aforementioned conventional techniques, the purpose of the present invention is to provide a mask inspection device and the method thereof to solve the current technical problems.

For its purpose, the present invention provides a mask inspection device, which comprises an inspection base, a shift platform, a rotating platform, a bearing platform, a laser ranging module, a vertical shift module, a processing module, and an image capturing module. An arched support is disposed on a surface of the inspection base. The shift platform is disposed on the same surface of the inspection base and is located between the inspection base and the arched support. The shift platform moves in the first direction along the inspection base. The rotating platform is disposed on the shift platform and moves in the second direction along the shift platform. The bearing platform is disposed on a surface of the rotating platform and holds and carries a mask. The mask comprises a substrate, a frame, and a dust-proof film. The frame is disposed on a surface of the substrate, and the dust-proof film is disposed on the frame. The laser ranging module is disposed on one side of the arched support and generates a distance measuring signal corresponding to an inspection region of the dust-proof film. The vertical shift module is disposed on the same side of the arched support. The processing module controls the vertical shift module to move upward or downward based on the distance measuring signal. The image capturing module is nearby the laser ranging module and is disposed on the vertical shift module. After the vertical shift module moves upward or downward, the image capturing module captures an inspection image of the inspection region that is measured by the laser ranging module. After the image capturing module captures the inspection image of one of the inspection regions, the shift platform moves to carry the next one of the plurality of inspection regions to a position corresponding to the laser ranging module and the image capturing module for generating the distance measuring signal and the inspection image of the next one of the plurality of inspection regions, and the processing module generates a height information of the dust-proof film based on the plurality of distance measuring signals and generates an inspection information based on the inspection images.

Preferably, the shift platform can comprise a guide track, and the rotating platform moves along the guide track.

Preferably, the first direction and the second direction can be perpendicular to each other.

Preferably, the vertical shift module can move in the direction perpendicular to the shift platform.

Preferably, the inspection information can comprise particle locations, particle sizes, or a combination thereof.

For its purpose, the present invention also provides a mask inspection method, which is applicable to the aforementioned mask inspection device, comprising the steps of: measuring one of the inspection regions of the dust-proof film of the mask at a default position and correspondingly generating a distance measuring signal; controlling the image capturing module disposed on the vertical shift module to move upward or downward based on the distance measuring signal; capturing the inspection image of the inspection region corresponding to the distance measuring signal; carrying another inspection region to the default position by the shift platform and, correspondingly, generating the distance measuring signal and capturing the inspection image; after the plurality of inspection regions are measured, generating the height information of the dust-proof film based on the plurality of distance measuring signals; after the plurality of inspection images of the plurality of inspection regions are captured, generating the inspection information based on each inspection image.

Preferably, the shift platform can comprise a guide track, and the bearing platform, which carries and holds the mask, can move along the guide track.

In conclusion, in the mask inspection device and the method thereof in accordance with the present invention, before the image capturing module captures the image of one of the inspection regions, the laser ranging module measures this inspection region first, and the vertical shift module carrying the image capturing module then moves upward or downward to adjust its position based on the acquired distance measuring signal. As a result, the mask inspection device and the method thereof have the advantages of the precise inspection and, consequently, the lithography yield improvement.

DESCRIPTION OF THE PREFERRED EMBODIMENTS

Figure 1:
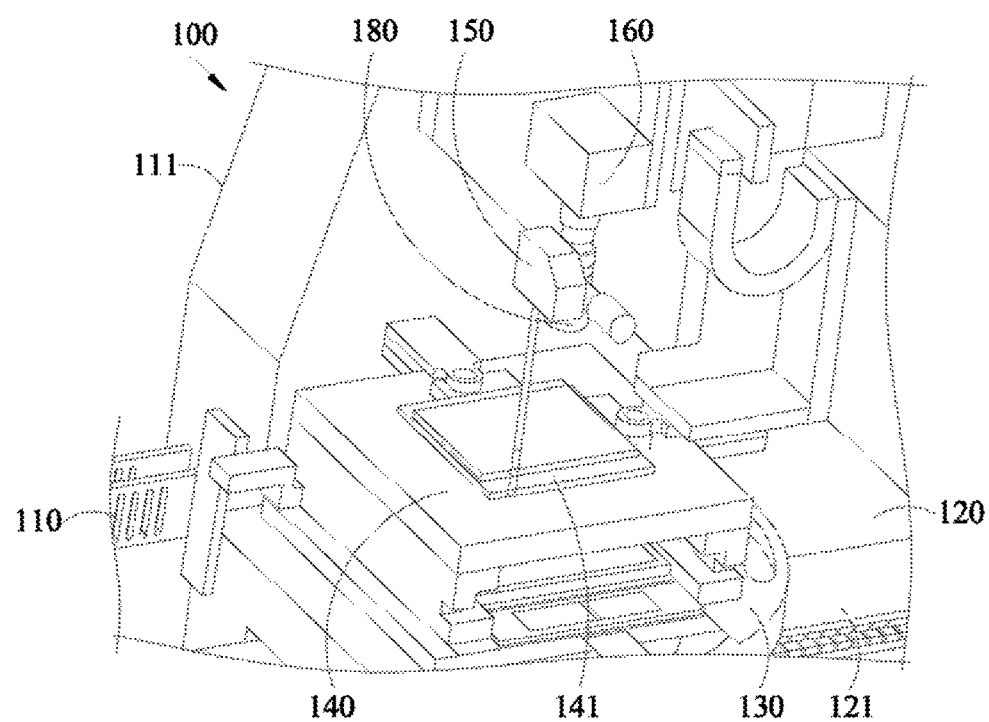
FIG. 1 is the schematic diagram showing the mask inspection device of the present invention.
Figure 2:
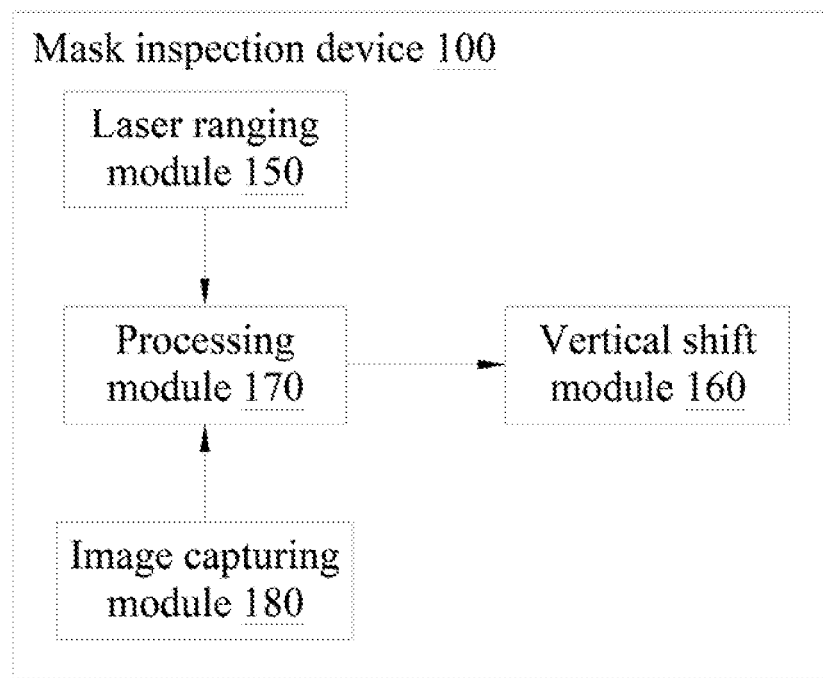
FIG. 2 is the block diagram showing the mask inspection device of the present invention.

For better understanding the technical features, the content, the advantages and the effects, the present invention will be presented hereinafter through embodiments accompanying with corresponding figures. Since being only for the illustrative and auxiliary purposes, the figures are not necessarily implying the actual ratio or precise configuration of the products of the present invention. Therefore, the claims of the present invention that are actually applied should not be limited by the figures' ratio and configuration.

In order to make it easier to comprehend the advantages, the features, and the approaches, the present invention will be described in detail with embodiments and their corresponding figures. The present invention can also be approached in different ways and should not be considered only limited by these embodiments. For one skilled in the art, the scope of the present invention can be more clearly, thoroughly, and completely delivered through these provided embodiments and is, however, defined solely by the appended claims.

Refer to FIGS. 1-4, which are respectively the schematic diagram, the block diagram, the first schematic diagram of the mask, and the second schematic diagram of the mask of the mask inspection device of the present invention. As shown in the figures, the mask inspection device 100 comprises an inspection base 110, a shift platform 120, a rotating platform 130, a bearing platform 140, a laser ranging module 150, a vertical shift module 160, a processing module 170, and an image capturing module 180. The shift platform 120 carries the bearing platform 140, which holds the mask 141, to move, such that each inspection region 104 of the dust-proof film 103 of the mask 141 sequentially moves to a position corresponding to the laser ranging module 150 and the image capturing module 180. The vertical shift module 160 carries the image capturing module 180 to move upward or downward. The processing module 170 controls the movement of shift platform 120 and the movement of the vertical shift module 160 and also analyzes inspection images and accordingly generates an inspection information. The processing module 170 also generates height information of the dust-proof film based on the plurality of distance measuring signals.

Furthermore, an arched support 111 is disposed on a surface of the inspection base 110. The shift platform 120 is disposed on the same surface of the inspection base 110 and is located between the inspection base 110 and the arched support 111. The arched support 111 transversely extends across the shift platform 120, which is movable in the first direction along the inspection base 110. The rotating platform 130 is disposed on the shift platform 120 and can move in the second direction along the shift platform 120, and the first direction is perpendicular to the second direction, such that, through the shift platform 120, the mask 141 can correspondingly move in the X-axis direction or Y-axis direction of the inspection base 110.

Figure 3:
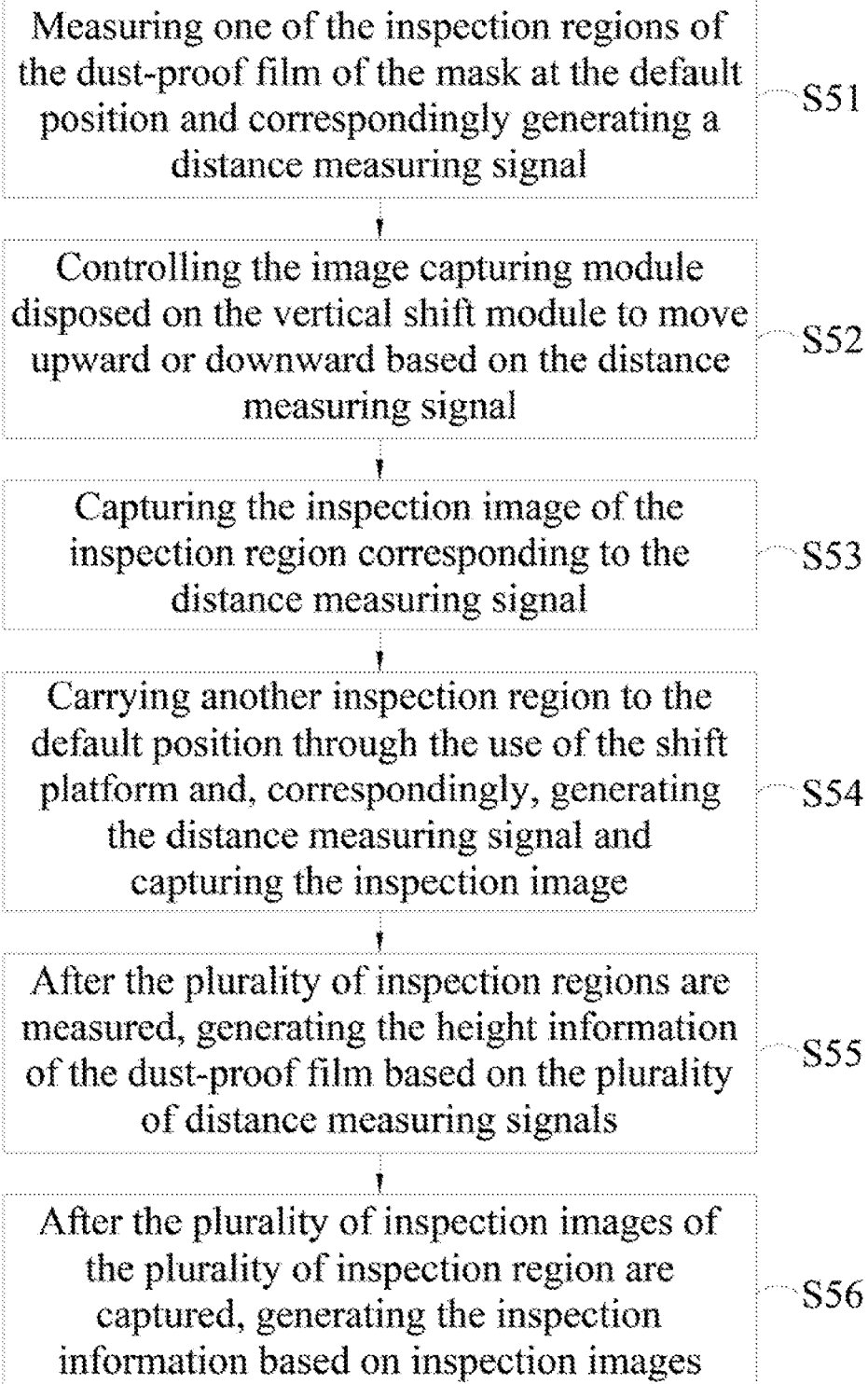
FIG. 3 is the first schematic diagram showing the mask of the mask inspection device of the present invention.

The bearing platform 140 is disposed on a surface of the rotating platform 130 and holds and carries the mask 141. As shown in FIG. 3, the mask 141 comprises a substrate 101, a frame 102, and a dust-proof film 103. The frame 102 is disposed on a surface of the substrate 101, and the dust-proof film 103 is disposed on the frame 102. On the dust-proof film 103, there are a plurality of inspection regions 104, which are objects for measuring and inspecting.

The laser ranging module 150, which is disposed on one side of the arched support 111, is utilized to perform inspections on the plurality of inspection regions 104 of the dust-proof film 103. The laser ranging module 150 correspondingly generates a distance measuring signal for each inspection region 104 of the dust-proof film 103. The vertical shift module 160 is also disposed on the same side of the arched support 111 as the laser ranging module 150. The processing module 170 controls the vertical shift module 160 to move upward or downward based on the distance measuring signal. The image capturing module 180 is nearby the laser ranging module 150 and is disposed on the vertical shift module 160. After the vertical shift module 160 moves upward or downward, the image capturing module 180 captures an inspection image of the inspection region 104 that is measured by the laser ranging module 150. Through the movement of the vertical shift module 160 controlled by the processing module 170, the distance between the inspection region 104 and the image capturing module 180 can be adjusted to match the focusing distance of the image capturing module 180. Preferably, the vertical shift module 160 moves vertically with respect to the shift platform 120, such that the image capturing module 180 moves upward and downward with respect to the dust-proof film 103.

After the image capturing module 180 taking the inspection image of one of the inspection regions 104, the shift platform 120 carries the next inspection region 104 to the position corresponding to the laser ranging module 150 and the image capturing module 180 for acquiring the distance measuring signal and the inspection image of this inspection region 104. In this way, the distance measuring signal and the inspection image of each inspection region 104 can be acquired for the processing module 170 to generate the height information of the dust-proof film 103 based on the plurality of distance measuring signals and to generate the inspection information based on each inspection image. The inspection information includes the information about the particles, such as particle locations, particle sizes, etc.

Furthermore, the shift platform 120 can further comprise a guide track 121, on which the rotating platform 130 can be disposed. In this way, the rotating platform 130 can move in the second direction along the guide track 121.

Figure 4:
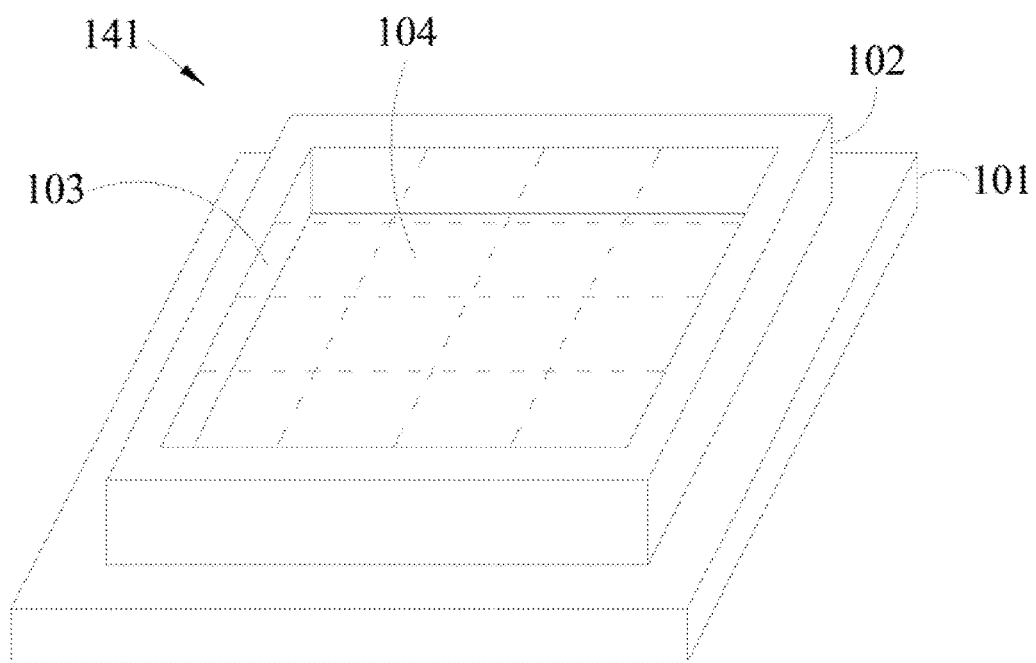
FIG. 4 is the second schematic diagram showing the mask of the mask inspection device of the present invention.

As shown in FIG. 4, a bulged dust-proof film 103 can happen if the gas confined in the space between the dust-proof film 103 and the substrate 101 expands due to the changing of the pressure. During the application of the mask 141, the bulged dust-proof film 103 may be broken and attached on the mask 141. In order to remove those masks 141 with a dust-proof film 103 being overly bulged, the laser ranging module 150 generates a distance measuring signal for each inspection region 104, and based on these distance measuring signals, the processing module 170 generates the height information about the dust-proof film 103. The height information can also be further processed by the processing module 170 so as to be shown graphically. In this way, the bulging condition of the dust-proof film 103 can be properly monitored.

In the previous description of the mask inspection device of the present invention, although the concept of the mask inspection method of the present invention has also already been mentioned, the flow chart of the method will be illustrated hereinafter for the purpose of clarification.

Figure 5:
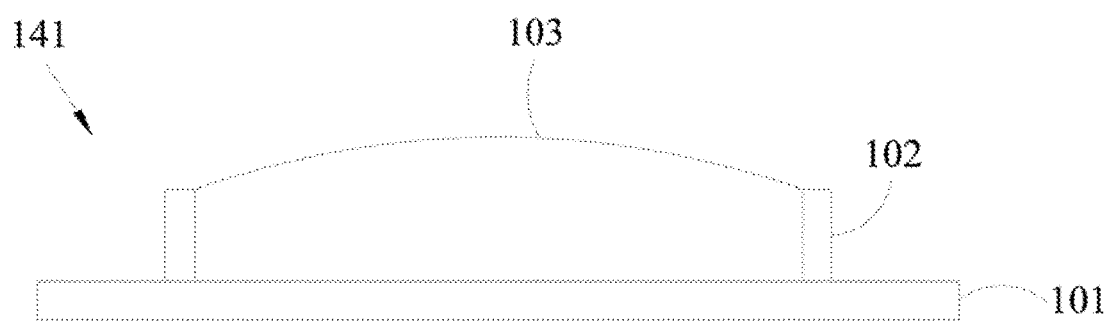
FIG. 5 is the flow chart representing the mask inspection method of the present invention.

Refer to FIG. 5, which is the flow chart representing the mask inspection method of the present invention. As shown in the figure, the mask inspection method of the present invention, which is applicable to the mentioned mask inspection device 100, comprises the steps of:

Step S51: measuring one of the inspection regions of the dust-proof film of the mask at the default position and correspondingly generating a distance measuring signal. The default position is the position that the laser ranging module can perform the measurement and the image capturing module can capture the inspection image.

Step S52: controlling the image capturing module disposed on the vertical shift module to move upward or downward based on the distance measuring signal.

Step S53: capturing the inspection image of the inspection region corresponding to the distance measuring signal.

Step S54: carrying another inspection region to the default position through the use of the shift platform and, correspondingly, generating the distance measuring signal and capturing the inspection image.

The steps S51-S54 are repeated until that all inspection regions are measured and inspected.

Step S55: after the plurality of inspection regions are measured, generating the height information of the dust-proof film based on the plurality of distance measuring signals.

Step S56: after the plurality of inspection images of the plurality of inspection region are captured, generating the inspection information based on inspection images.

In addition, the aforementioned shift platform can comprise a guide track, and the bearing platform, which holds the mask, can move along the guide track.

The detailed description and the practical embodiments of the mask inspection method of the present invention have already been covered in the previous description of the mask inspection device of the present invention. They are therefore skipped for the purpose of conciseness.

In conclusion, since an image of one of the inspection regions is taken after the laser ranging module measuring this inspection region, and the vertical shift module, which carries the image capturing module, moving upward or downward to adjust its position based on the acquired distance measuring signal, the mask inspection device and the method thereof of the present invention therefore have the advantages of the precise inspection and, consequently, the lithography yield improvement.

The purpose of described embodiments is to illustrate the technical ideas and features of the present invention, such that one skilled in the art can comprehend the contents of the present invention and can therefore practice said invention accordingly. It should be understood, however, that the invention is not to be limited to the particular form disclosed, but to the contrary, the invention is to cover all modifications, equivalents, and alternatives falling within the spirit and scope of the appended claims.

What is claimed is:

1. A mask inspection device, comprising:
    an inspection base, a surface of which is disposed with an arched support;
    a shift platform, which is disposed on the surface of the inspection base and is located between the inspection base and the arched support, wherein the shift platform moves in a first direction along the inspection base;
    a rotating platform, which is disposed on the shift platform and moves in a second direction along the shift platform;
    a bearing platform, which is disposed on a surface of the rotating platform and carries and holds a mask, wherein the mask comprises a substrate, a frame, and a dust-proof film, wherein the frame is disposed on a surface of the substrate and the dust-proof film is disposed on the frame;
    a laser ranging module, which is disposed on one side of the arched support and generates a distance measuring signal corresponding to one of a plurality of inspection regions of the dust-proof film;
    a vertical shift module, which is disposed on the one side of the arched support;
    a processing module, which controls the vertical shift module to move upward or downward based on the distance measuring signal; and
    an image capturing module, which is disposed on the vertical shift module and is nearby the laser ranging module, wherein the image capturing module captures an inspection image of the one of the plurality of inspection regions that is measured by the laser ranging module;
    wherein, after the image capturing module captures the inspection image of the one of the inspection regions, the shift platform moves to carry a next one of the plurality of inspection regions to a position corresponding to the laser ranging module and the image capturing module for generating the distance measuring signal and the inspection image of the next one of the plurality of inspection regions, and the processing module generates a height information of the dust-proof film based on the plurality of distance measuring signals and generates an inspection information based on inspection images.

2. The mask inspection device of claim 1, wherein the shift platform comprises a guide track, and the rotating platform moves along the guide track.

3. The mask inspection device of claim 1, wherein the first direction is perpendicular to the second direction.

4. The mask inspection device of claim 1, wherein the vertical shift module moves in a direction being perpendicular to the shift platform.

5. The mask inspection device of claim 1, wherein the inspection information comprises a particle location, a particle size, or a combination thereof.

6. A mask inspection method, which is applicable to the mask inspection device of claim 1, comprising the steps of:
    measuring one of a plurality of inspection regions of a dust-proof film of a mask at a default position and accordingly generating a distance measuring signal;
    controlling an image capturing module on a vertical shift module to move upward or downward based on the distance measuring signal;
    capturing an inspection image of the one of the plurality of inspection regions corresponding to the distance measuring signal;
    carrying an another inspection region to the default position by a shift platform and, correspondingly, generating the distance measuring signal and capturing the inspection image;

after the plurality of inspection regions are measured, generating height information of the dust-proof film based on the plurality of distance measuring signals; and after the plurality of inspection images of the plurality of inspection regions are captured, generating inspection information based on the plurality of inspection images.

7. The mask inspection method of claim 6, wherein the shift platform comprises a guide track, and a bearing platform configured to carry and hold the mask is movable along the guide track.

8. The mask inspection method of claim 6, wherein the vertical shift module moves in a direction perpendicular to the shift platform.

9. The mask inspection method of claim 6, wherein the inspection information comprises a particle location, a particle size, or a combination thereof.

* * * * *